United States Patent
Bullock et al.

(10) Patent No.: US 7,356,364 B1
(45) Date of Patent: Apr. 8, 2008

(54) DEVICE FOR OPTICAL MONITORING OF CONSTITUENT IN TISSUE OR BODY FLUID SAMPLE USING WAVELENGTH MODULATION SPECTROSCOPY, SUCH AS FOR BLOOD GLUCOSE LEVELS

(75) Inventors: Audra M. Bullock, Kaneohe, HI (US); Daniel F. Ling, Honolulu, HI (US); John Roeder, Mililani, HI (US); Hao Chih Ho, Honolulu, HI (US); Anita Schorlemmer, Honolulu, HI (US)

(73) Assignee: University of Hawai'i, Honolulu, HI (US)

( * ) Notice: Subject to any disclaimer, the term of this patent is extended or adjusted under 35 U.S.C. 154(b) by 598 days.

(21) Appl. No.: 11/041,168

(22) Filed: Jan. 21, 2005

Related U.S. Application Data

(60) Provisional application No. 60/632,300, filed on Nov. 30, 2004, provisional application No. 60/538,988, filed on Jan. 23, 2004.

(51) Int. Cl.
*A61B 5/00* (2006.01)
(52) U.S. Cl. .................. 600/310; 600/316; 600/322; 604/67
(58) Field of Classification Search ............... 600/309, 600/310, 316, 322
See application file for complete search history.

(56) References Cited

U.S. PATENT DOCUMENTS

| | | | |
|---|---|---|---|
| 2,004,957 A | 6/1935 | Messner | |
| 2,778,045 A | 1/1957 | Bly et al. | |
| 4,427,116 A | 1/1984 | Brown | |
| 5,315,993 A * | 5/1994 | Alcala | 600/341 |
| 5,433,952 A | 7/1995 | Sipos | |
| 5,919,134 A * | 7/1999 | Diab | 600/323 |
| D434,137 S | 11/2000 | Davis | |
| 6,351,309 B1 * | 2/2002 | Bomse et al. | 356/437 |
| 6,524,023 B2 | 2/2003 | Andersen | |
| 2003/0050544 A1 * | 3/2003 | Routt et al. | 600/318 |

* cited by examiner

*Primary Examiner*—Eric Winakur
*Assistant Examiner*—Etsub D Berhanu
(74) *Attorney, Agent, or Firm*—Leighton K. Chong

(57) ABSTRACT

A device for monitoring the concentration level of a constituent in tissue or a body fluid sample, such as glucose concentration in blood, has a laser light source which is modulated about a center emission frequency to probe the absorption spectrum of the constituent being monitored, a laser driver circuit for tuning and modulating the laser light, a photodetector for detecting light from the laser light source transmitted through the sample as the modulation frequency of the laser is tuned, and a demodulator for demodulating the transmitted light and detecting variations in magnitude at harmonics of the modulation frequency to assess the concentration level of that constituent. The device utilizes short-wavelength near-infrared laser light to monitor blood glucose levels, and could also be used for drug screening and diagnosis of other medical conditions as well. In one embodiment, the device is used to monitor blood glucose level externally from the body and non-invasively by transillumination through a thin layer of skin, without the need for physical penetration of the skin. In another embodiment, the device is used as an intravenous sensor deployed through a catheter, and its output can be used to control an insulin pump to stabilize the patient's blood glucose levels.

20 Claims, 17 Drawing Sheets

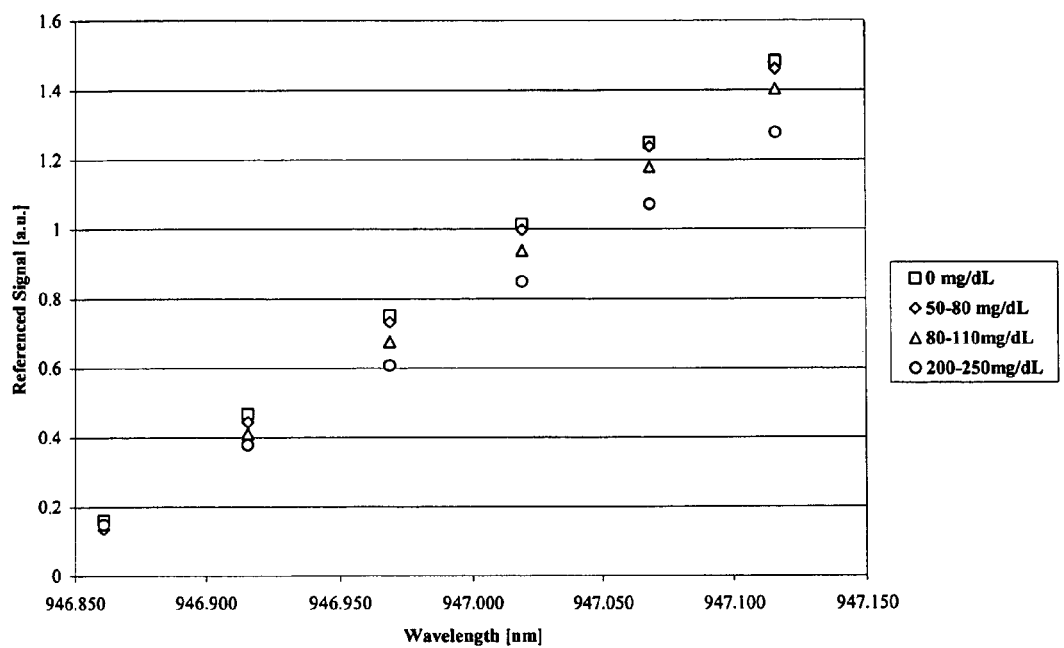
Figure 6a  Direct Transmission Locked Signal
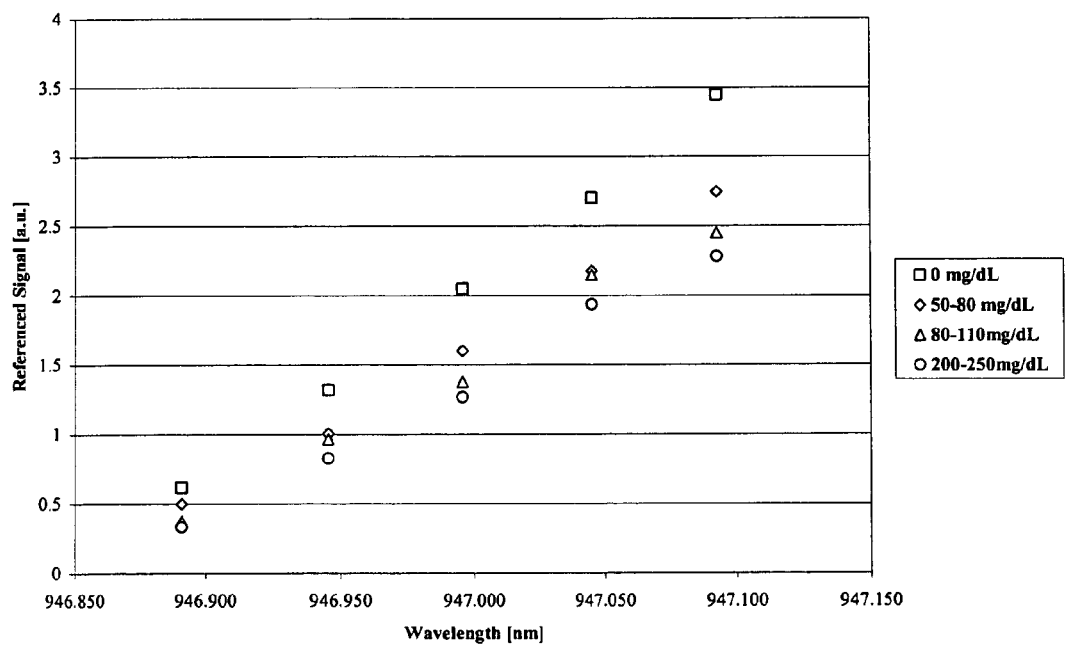
Figure 6b  Second Harmonic Locked Signal Direct Transmission Signal First Harmonic Signal

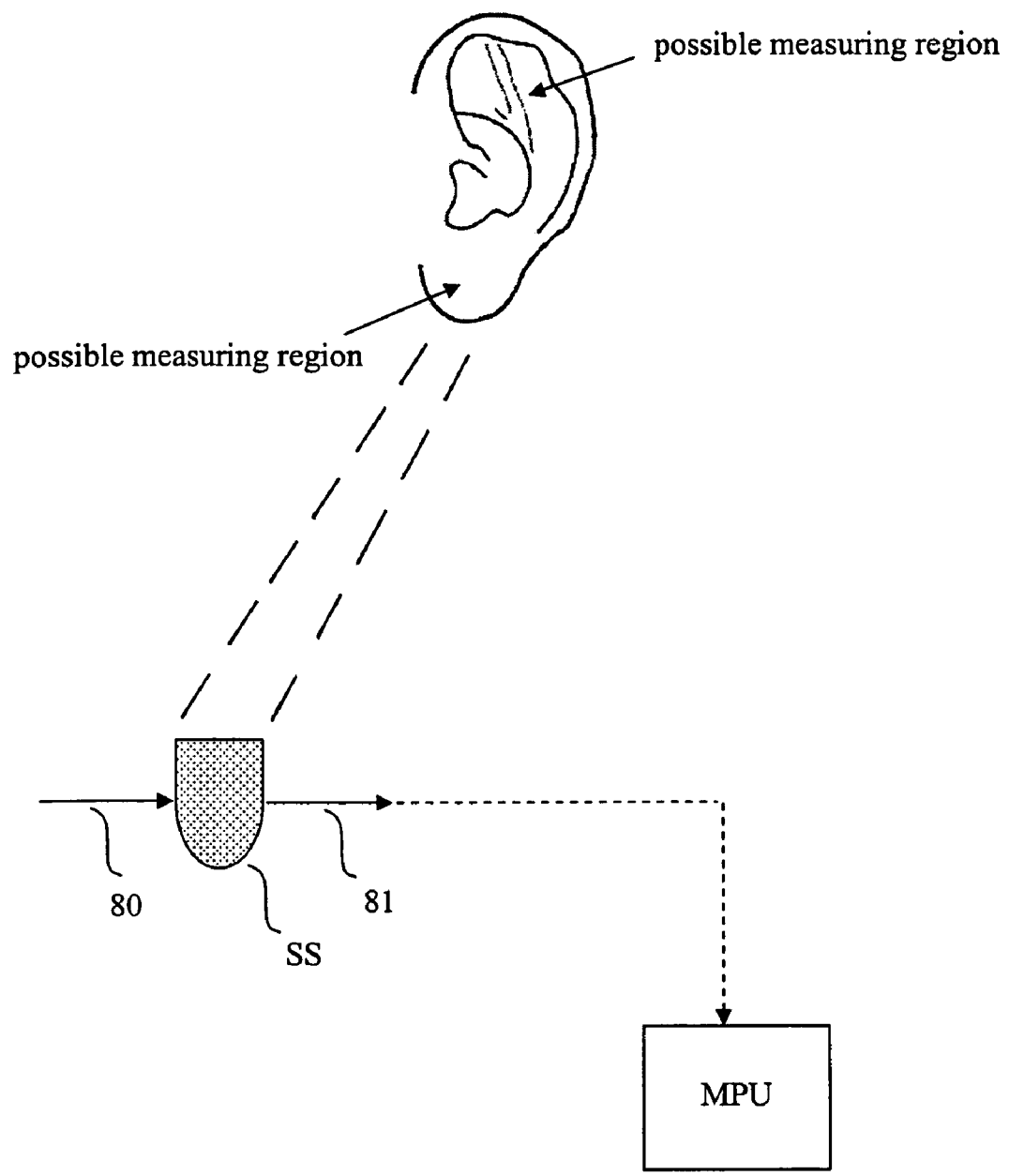

DEVICE FOR OPTICAL MONITORING OF CONSTITUENT IN TISSUE OR BODY FLUID SAMPLE USING WAVELENGTH MODULATION SPECTROSCOPY, SUCH AS FOR BLOOD GLUCOSE LEVELS

This U.S. patent application claims the priority of U.S. Provisional Application No. 60/538,988 filed on Jan. 23, 2004, entitled "Non-Invasive Biomedical Sensor", and U.S. Provisional Application No. 60/632,300, filed on Nov. 30, 2004, entitled "Continuous Intravenous Optical Glucose Monitor with Feedback Control for Insulin Pump", of the same inventors.

The subject matter herein was developed in part under a research grant provided by the U.S. Government, National Science Foundations, Grant/Project No. ECS01-34640, ORS No. R-2001906. The U.S. Government retains certain rights in the invention.

TECHNICAL FIELD

This invention generally relates to a device for optical monitoring of a constituent in tissue or body fluid sample, particularly for non-invasive or intravenous blood glucose monitoring.

BACKGROUND OF INVENTION

According to the American Diabetes Association, over 6% of the US population is affected by diabetes. Worldwide, the number of people with diabetes is increasing at an astounding rate and is predicted reach epidemic proportions. Commercially available methods of monitoring glucose levels are invasive and prone to error. For many individuals, monitoring must be performed frequently throughout the day. The pain and risk of infection from invasive probes can often deter them from maintaining their prescribed monitoring schedule, escalating the risks of secondary aliments of diabetes mellitus. It would be desirable to alleviate the pain and risks for individuals who must routinely monitor their body chemistry by developing a device that accurately characterizes aqueous biological samples, such as urine, blood, saliva, or other bodily fluids, in a non-invasive manner. Current research has focused on optical identification of glucose levels in urine within the short-wavelength near infrared (sw-NIR) spectrum.

Noninvasive analyte monitoring using optical techniques are well known in the prior art. For example, U.S. Pat. No. 6,377,828 issued Apr. 23, 2002, to Chaiken discloses using the Raman spectra emitted by a tissue after excitation with a first wavelength equal to the absorption frequency of a temperature probe, hemoglobin, and a second wavelength equal to the absorption frequency of the analyte, in order to measure blood glucose concentrations. U.S. Pat. No. 6,640,116 issued Oct. 28, 2003, to Diab discloses use of Faraday rotation measurements (polarization of the incident beam by a magnetic field) through tissue for glucose measurement. Also, U.S. Pat. No. 6,445,938 issued Sep. 3, 2002, to Berman et al discloses a device that uses attenuated total reflection (ATR) infrared spectroscopy on the patient's fingertip for monitoring glucose levels in the body based on analyses of unique IR signatures.

It has also been known to provide an implantable light sensor in vivo for monitoring blood glucose levels. For example, U.S. Pat. No. 6,122,536 issued Sep. 19, 2000, to Sun, et al. discloses an infrared light sensor surgically implanted around a blood vessel, puncturing each side of the vessel, for continuously monitoring a blood constituent such as glucose by discriminating among different spectral bands having a unique temporal or frequency modulation. U.S. Pat. No. 6,097,975 issued Aug. 1, 2000, to Petrovsky, et al. measures blood glucose concentration by projecting a pulse of light through an optical fiber onto a blood-vessel-rich area of the body (such as the inner wrist, elbow or ear lobe). U.S. Pat. No. 6,016,435 issued Jan. 18, 2000, to Maruo, et al. discloses the analysis of NIR light received in a light-receiving unit positioned in the) dermis layer of skin, based on statistically correlating glucose concentration detected in the dermis region with that of test subjects.

Other prior art involving the use of light in the near-infrared (NIR) range for monitoring blood glucose concentration includes U.S. Pat. No. 5,070,874 to Barnes, et al., U.S. Pat. No. 5,360,004 to Purdy et al., and U.S. Pat. No. 5,267,152 to Yang et al. Diffusive reflectance NIR spectroscopy is also disclosed in U.S. Pat. No. 5,910,109 to Peters, et al., International Patent Publication WO 0216905, U.S. Pat. No. 6,152,876 assigned to Rio Grande Medical Technologies Inc., U.S. Pat. No. 5,945,676 assigned to Sensys Medical, and U.S. Pat. Nos. 5,086,229 and 5,028,787 to Rosenthal, et al. Spectral analysis of a polychromatic light source for noninvasive measurement of blood glucose is disclosed in U.S. Pat. No. 5,361,758 to Hall, et al.

However, such prior art devices have limitations that prevent their widespread use, e.g., lack of sensitivity and specificity, interference with other blood constituents and noise limitations. Conventional noninvasive sensor systems for blood glucose monitoring still require frequent "finger-stick" blood glucose measurements for recalibration purposes, thus defeating its purpose to replace invasive methods.

U.S. Pat. No. 5,533,509 issued Jul. 9, 1996, to Koashi, et al. teaches noninvasive blood glucose monitoring using wavelength modulated light, in which the intensity of transmitted or reflected light as well as the intensity of incident light is detected, then the ratio of the two intensities and the rate of change in the ratio with respect to the change in the wavelength are determined. The derivative of the absorption spectrum of glucose is extracted and the blood sugar of that portion based on these derivative spectra for all modulating intensities of light is detected, so that derivative data of high quality is obtained in real time without requiring computer processing. However, this system is lacking in spectral referencing to completely eliminate spectral drifting of the optical system, and in the proper rationing of higher order derivative features to provide absolute glucose concentrations in varying portions of tissues.

One of the largest obstacles in non-invasive biomedical sensing is variability in the samples from person to person and from day to day. Numerous variables must be analyzed simultaneously, requiring long and complex multivariate calculations to provide precise measurements of constituents. The primary limitation of the multivariate analysis used in conventional measurement techniques is that if one of the components is estimated incorrectly, then the whole analysis can be skewed. This inherent problem can be difficult to isolate and correct in real-time.

SUMMARY OF INVENTION

In accordance with the present invention, the issues plaguing conventional non-invasive biomedical sensors are overcome by a device which can monitor a constituent in an aqueous sample by employing wavelength-modulation absorption spectroscopy of a laser light probe, and active signal processing and filtering to spectrally stabilize the laser probe, increase the signal-to-noise ratio, and decrease the calculations required.

In accordance with the invention, a device for monitoring the concentration level of a constituent in tissue or a body fluid sample comprises:

(a) a laser light source in which the light is frequency modulated about a center emission frequency selected to probe a characteristic feature in an absorption spectrum of a constituent of the sample to be monitored;

(b) a laser driver circuit, operatively coupled to said laser light source, for controlling the frequency modulation of the laser light and tuning the center emission frequency of the laser light through a desired region of the absorption spectrum of said constituent;

(c) a photodetector for detecting light from the laser light source transmitted through the sample as the modulation emission frequency of the laser is tuned; and (d) a demodulator for demodulating the transmitted light and detecting variations in magnitude at harmonics of the modulation frequency so as to assess the concentration level of the constituent of the sample.

In a preferred embodiment, a single-mode laser is modulated about a center wavelength to probe a weakly absorbing constituent of the sample being monitored. The laser radiation is passed through the sample as the center wavelength of the laser is tuned in a stepwise manner through spectral control of a laser emission control device known as an etalon. The interaction of the wavelength-modulated probe with the absorption feature leads to a transmitted signal, whose magnitude varies at harmonics of the modulation frequency. The transmitted light is detected by a photodiode and the harmonics are demodulated using phase-sensitive coherent detection. The resulting set of demodulated signals (one signal at each detectable harmonic) provides information on the absorber, including species identification, concentration, and temperature.

The key advantages of this technique are that it exploits the noise reduction associated with coherent detection, allows for referencing and spectral stabilization, and enhances the spectral signature derived by harmonic detection. Furthermore, this measurement technique is conveniently implemented with semiconductor lasers, allowing the device to be constructed for a fraction of the cost of competitive optical systems. Many available laser diode geometries, including edge-emitting lasers and vertical-cavity surface emitting lasers (VCSELs), can be tuned and modulated (both amplitude and wavelength) via injection current. Both heterojunction edge-emitting lasers and VCSELs can be employed for non-invasive sensing.

In a particular embodiment, the monitoring device is used to monitor blood glucose concentrations externally from the body and non-invasively by transillumination of the photodiode through a thin layer of skin, such as the earlobe or finger webbing, upon which a portion of the light is transmitted through the skin. The transmitted light is detected by a photodetector, spectrally analyzed, and processed by a microprocessor to measure quantitatively and accurately the patient's blood glucose concentration, without the need for physical penetration of the skin. This device can be made portable and conveniently used at home or at any location by people who suffer from diabetes to continuously or periodically monitor blood glucose levels while avoiding the need for finger lancing as is done conventionally. The device can similarly be used to monitor other blood constituents, such as carbon dioxide, hemoglobin, potassium, etc.

In another particular embodiment, the monitoring device is used as an intravenous sensor for continuously monitoring blood glucose levels of patients through a catheter or other probe deployed intravenously. The device uses a laser diode to deliver light to the catheter probe end and collects light transmitted through the blood in contact with the probe by an optical fiber and reflector end deployed in opposition to one another. The light is collected by the optical fiber and routed back to the photodiode by an optical circulating element. The transmitted light is spectrally analyzed and processed by a microprocessor in seconds to measure the patient's blood glucose levels. The system can be used to regulate blood glucose levels in critically ill patients who suffer from hyperglycemia, where self-regulation of glucose and insulin levels might otherwise fail or require constant nursing attention. This is done by using the detection level output to control an insulin pump to stabilize the patient's glucose concentration within a desired range, such as 80-110 mg/dL. The device can similarly be used to monitor other blood constituents, such as carbon dioxide, hemoglobin, potassium, etc.

Other objects, features, and advantages of the present invention will be explained in the following detailed description of the invention having reference to the appended drawings.

BRIEF DESCRIPTION OF DRAWINGS

FIGS. 2a to 2d illustrate the light transmission spectra of the first to fourth harmonics, respectively, of the wavelength modulation spectroscopy system.

FIGS. 6a to 6c show comparisons of direct, second and fourth harmonic signals for a saline control and different levels of glucose mixtures.

FIG. 8 illustrates the use of an external laser probe to transmit frequency-modulated laser light harmlessly through a thin layer of skin, such as the earlobe or finger webbing, for detection of blood glucose levels in blood vessels in the skin.

DETAILED DESCRIPTION OF INVENTION

Figure 1:
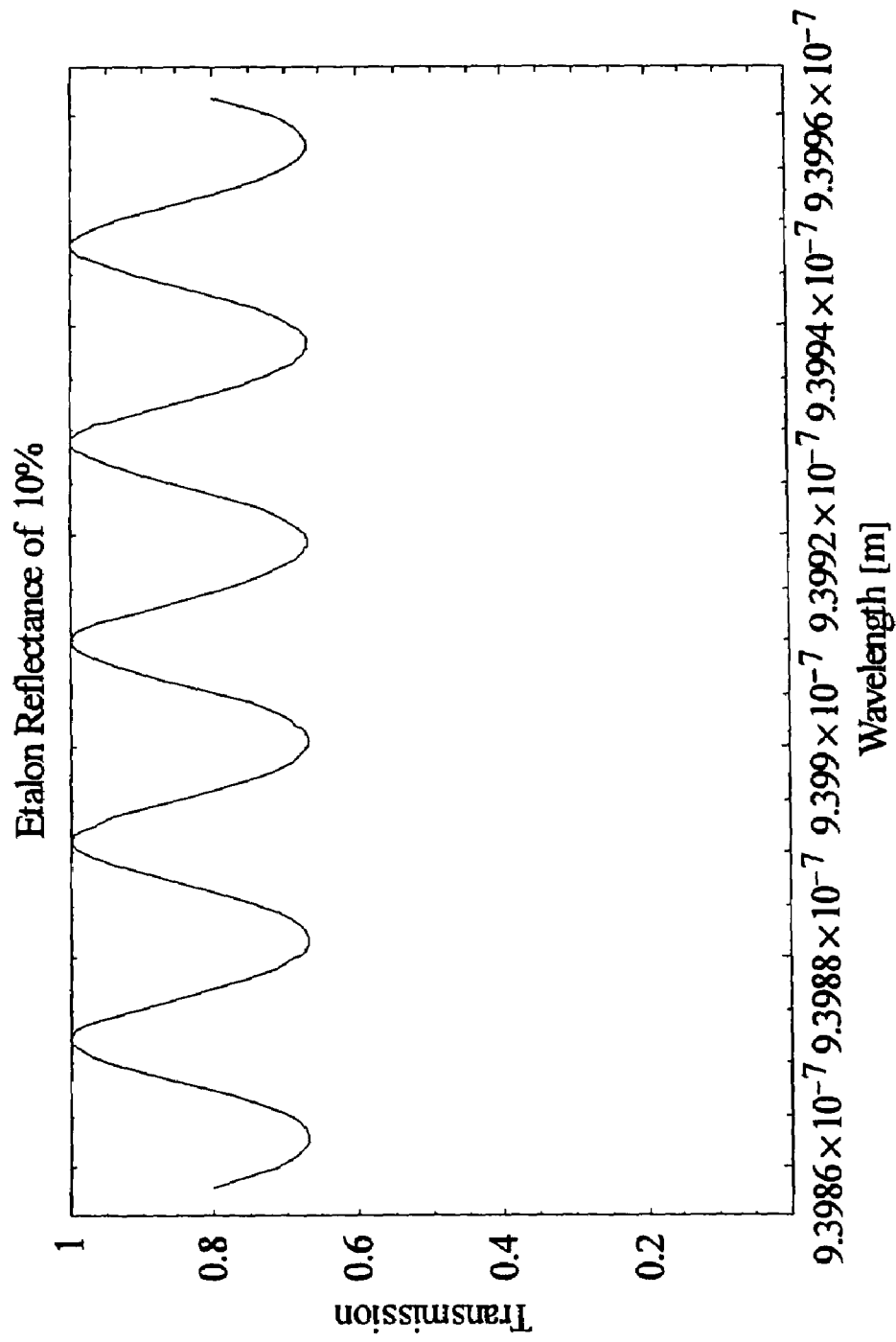
FIG. 1 is an illustration of light transmission profile versus wavelength for near-infrared (NIR) light in an optical monitoring system in accordance with the present invention.
Figure 2A:
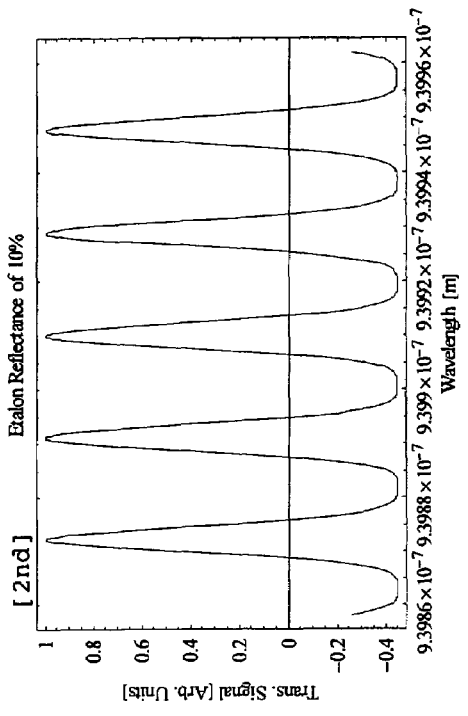
Figure 2A:
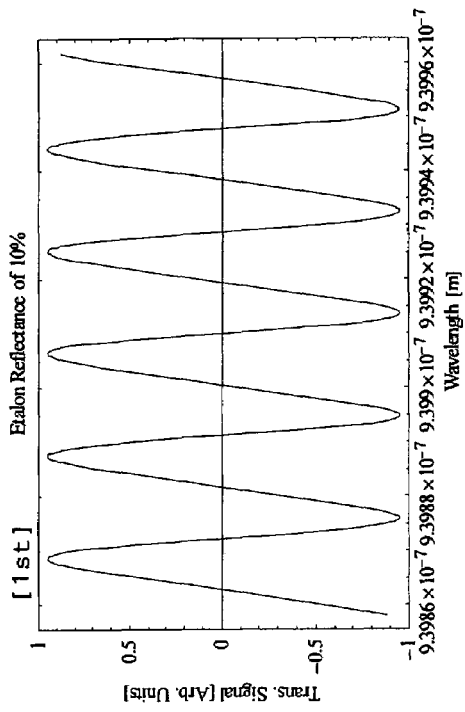
Figure 2B:
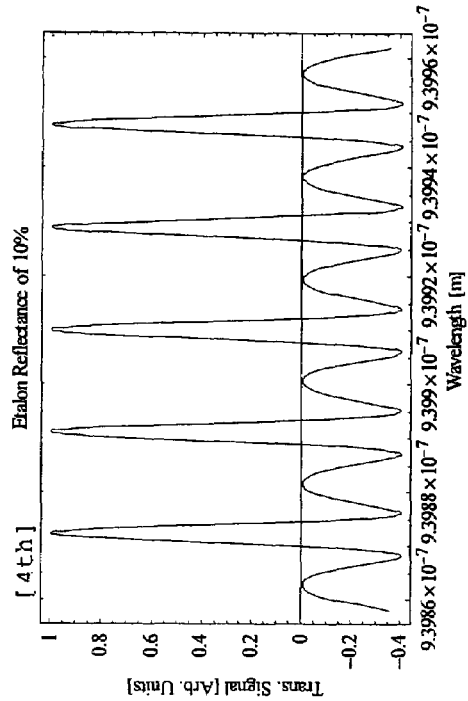
Figure 2C:
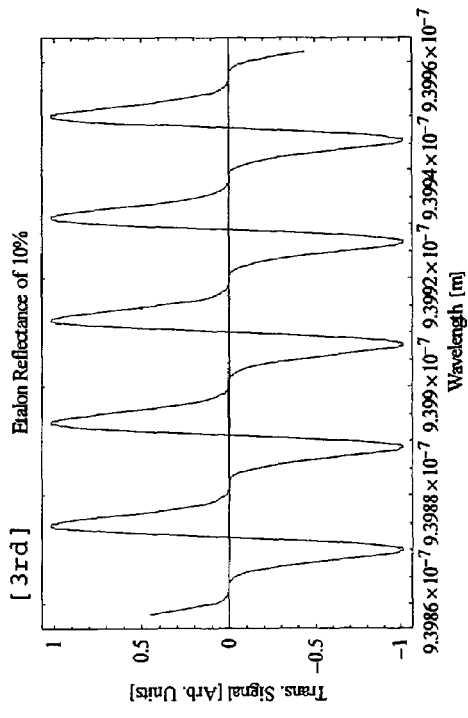
Figure 3B:
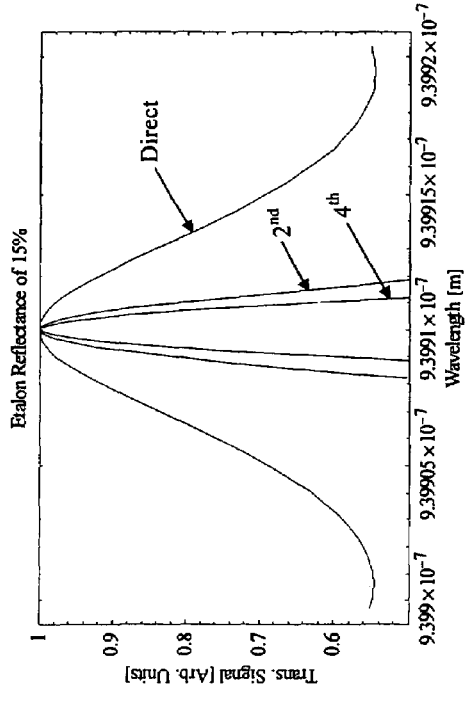
FIGS. 3a to 3d show a comparison of the transmission spectra of the even ($2^{nd}$ and $4^{th}$) harmonic signals for etalon cavities of 10%, 15%, 20%, and 30% reflectance, respectively.
Figure 3D:
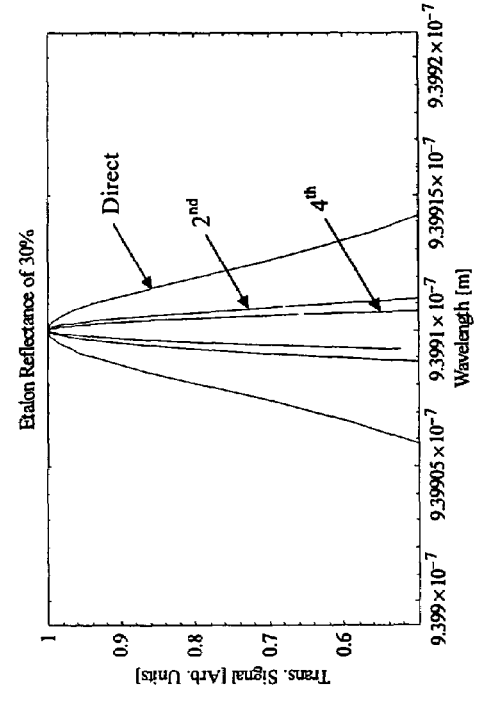
Figure 3A:
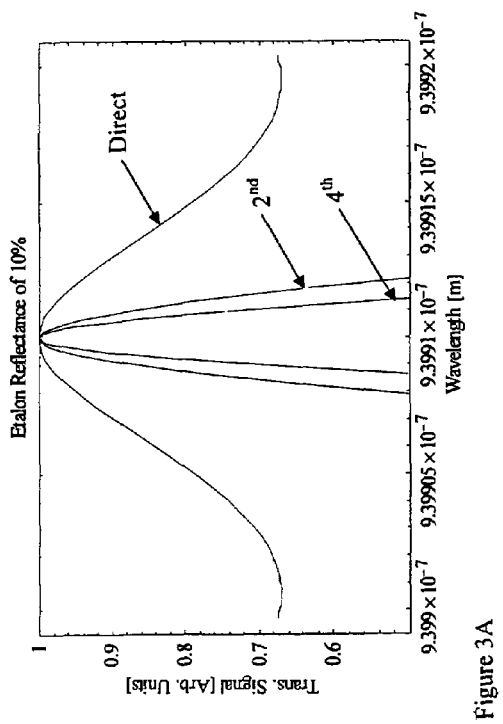
Figure 3C:
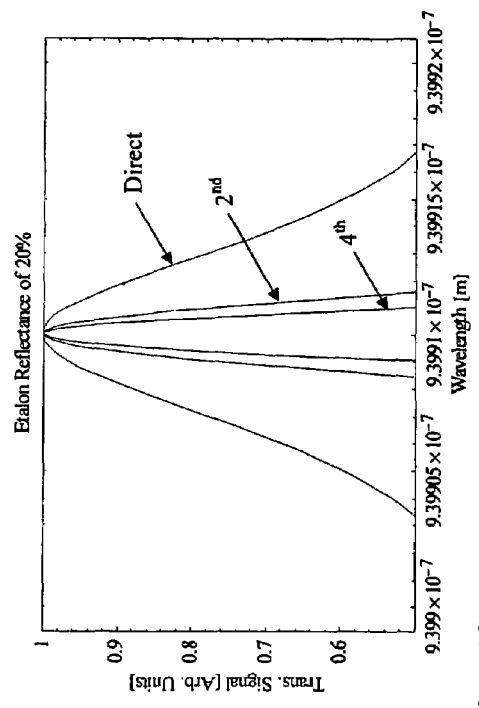

A preferred embodiment of the invention is described which provides a novel, cost-effective means of discrete frequency tuning and stabilization for semiconductor lasers. The principles of the experimental design are explored and the experimental apparatus is described. Preliminary data are given demonstrating the utility of the non-invasive technique presented here and showing indications of glucose absorption in the short-wavelength near infrared region of the spectrum.

Modulation spectroscopy is a relatively well-known technique; yet, its benefits have only begun to be realized. The most common motivation for employing modulation in spectroscopy is the noise reduction associated with coherent detection. While this is an attractive attribute, it is not the only benefit gained by employing modulation, particularly when the format is wavelength modulation. Wavelength modulation affords a host of additional advantages to be exploited in spectroscopic measurements, including improved sensitivity to concentration fluctuations, enhancement of spectral features, and multiple harmonic analyses. Further, wavelength modulation is easily performed with semiconductor lasers through modulation of the injection current. Thus, with the broad spectral coverage of commercial semiconductor lasers, wavelength modulation spectroscopy is a very convenient technique to use in optical sensing applications. The invention described herein employs wavelength modulation spectroscopy for laser stabilization and enhanced resolution of spectral features.

The key to exploiting the benefits of wavelength modulation spectroscopy is understanding the signal structure and its relationship to the depth of modulation. In the case of a small modulation depth, the wavelength modulation spectroscopy signal takes on a derivative like structure and can be modeled to first-order as such. This behavior can be realized by a simple Taylor series expansion of the frequency dependent absorption profile given a sinusoidal modulation. Consider a spectral signature $\alpha(\omega)$ that is probed by light with a sinusoidal frequency (or equivalently wavelength) modulation, $\omega=\omega_0+\beta \cos \omega_m t$, where $\omega_0$ is the center frequency of the light probe, $\omega_m$ is the modulation frequency, and $\beta$ is the amplitude, or depth, of the modulation. Thus, a Taylor series expansion of $\alpha(\omega)$ about $\omega_0$ gives:

$$\alpha(\omega_0 + \beta\cos\omega_m t) = \alpha(\omega_0) + \frac{d\alpha(\omega_0)}{d\omega}[\beta\cos\omega_m t] + \frac{d^2\alpha(\omega_0)}{d\omega^2}\frac{1}{2!}[\beta\cos\omega_m t]^2 + \frac{d^3\alpha(\omega_0)}{d\omega^3}\frac{1}{3!}[\beta\cos\omega_m t]^3 + K. \quad (1)$$

Expansion gives:

$$\alpha(\omega) = \left(\alpha^{(0)} + \alpha^{(2)}\frac{\beta^2}{4} + \alpha^{(4)}\frac{\beta^4}{64} + K\right) + \quad (2)$$
$$\left(\alpha^{(1)}\beta + \alpha^{(3)}\frac{\beta^{(3)}}{8} + \alpha^{(5)}\frac{\beta^{(5)}}{240} + K\right)\cos\omega_m t +$$
$$\left(\alpha^{(2)}\frac{\beta^{(2)}}{4} + \alpha^{(4)}\frac{\beta^4}{96} + \alpha^{(6)}\frac{11\beta^{(6)}}{23040}K\right)\cos2\omega_m t +$$
$$\left(\alpha^{(3)}\frac{\beta^3}{24} + \alpha^{(5)}\frac{\beta^5}{640} + \alpha^{(7)}\frac{\beta^7}{21504} + K\right)\cos3\omega_m t + \Lambda$$

In Equation (2) above, the derivative orders are designated by the superscript numerals in parentheses. Inspection of this equation shows two important aspects of the wavelength modulation spectroscopy technique. First, probing a spectral feature with a sinusoidal frequency probe creates a signal that varies at the harmonics of the modulation frequency. Second, when $\beta<1$, the component of the signal at the $N^{th}$ harmonic is primarily proportional to the $N^{th}$ derivative of the spectral profile. Note that in the limit of $\beta$ going to zero, pure derivatives result. This derivative nature is particularly beneficial in spectroscopy of continuous spectra, such as that of aqueous solutions or solid tissues, because gradual changes in the absorption spectrum will show up as more rapid variations in the harmonic components, especially at the higher harmonics. The disadvantage of using this type of harmonic analysis is that the signal magnitude at a given harmonics decreases as the harmonic order increases. Thus, there is a limit on the highest harmonic order one can detect. However, achieving a signal-to-noise of 50 or greater at the $9^{th}$ harmonic is reasonably easy to achieve with digital signal processing.

There is an upper limit on the modulation amplitude, $\beta$, for obtaining the derivative effect, which is defined by its relationship to the variation of the spectral feature. That is to say, as long as the frequency spectrum of the probe is less than the frequency span of the absorption feature being probed, a derivative-like signal emerges. Consequently, the key to applying this technique is optimizing the modulation amplitude for the spectral feature being probed, as well as for achieving a good signal-to-noise at the desired harmonic. For further details on this measurement technique, reference is made to: D. S. Bomse, A. C. Stanton, and J. A. Silver, Applied Optics 31, 718-731 (1992); J. M. Supplee, E. A. Whittaker, and W. Lenth, Applied Optics 33, 6294-6302 (1994); and A. N. Dharamsi and A. M. Bullock, "*Diode laser modulation spectroscopy and its applications*", Proc. of the International Conference on Lasers, p. 312-328, Portland, Oreg. (1996).

To employ wavelength modulation spectroscopy for blood glucose monitoring, there are two spectral features of interest: the glucose signature and the transmission spectrum of the Fabry-Perot etalon that is used for laser stabilization and tuning. A mechanism for laser stabilization is discussed in the following section.

Laser Stabilization and Tuning

Stabilization of the laser emission frequency is imperative for measurement fidelity and good a signal-to-noise ratio. Techniques for frequency stabilizing a laser often involve locking to a gas transition, locking to a stabilized Fabry-Perot etalon, or more novel techniques, such as locking via spectra hole burning in a solid-state material, for example, as demonstrated in the reference, P. B. Sellin, N. M. Strickland, J. L. Carlten, and R. L. Cone, "*Programmable frequency reference for subkilohertz laser stabilization by use of persistent spectral hole burning*", Optics Lett. 24, 1038-1040 (1999). The flexibility associated with Fabry-Perot etalons is particularly attractive for the system presented here, since we are probing an aqueous solution that must be sampled at periodically spaced points within the spectrum. Locking to the periodic resonances of an etalon allows us to achieve the discrete, stabilized tuning required for our measurements. However, cost is a primary issue and commercial etalons can be quite expensive. Locking to gas transitions is more cost effective, yet the locking is restricted to the available transitions and is not suitable for our system. Even though the degree of stabilization required for this experiment is not very stringent (100 Megahertz), the cost of purchasing an etalon with sufficient cavity finesse for this stability might preclude its use. Nevertheless, we were able to achieve the required level of stabilization with a lower quality etalon with partial reflectors used in common CD players though use of wavelength modulation and harmonic detection.

To illustrate, consider the transmission spectrum, T, of a Fabry-Perot cavity with reflection coefficient, R, for each surface, and length d:

$$T = \left[1 + \frac{4R}{1-R^2}\sin^2\frac{\phi}{2}\right]^{-1}, \text{ where } \phi = \frac{2\pi}{\lambda}2nd\cos\theta_1, \quad (3)$$

n is the refractive index of the material between the reflective surfaces, and $\theta_1$ is the angle of incidence. For our system, we constructed an air-filled etalon from two partial reflectors having reflection coefficient of 10% for both faces, separated by 23.4 mm.

FIG. 1 is an illustration of light transmission profile versus wavelength (Eq. 3) for a low-quality cavity, at normal (10%) incidence, within an sw-NIR spectral region of interest (centered at about 940 nm). Rather than the well-defined peaks obtained from most commercial etalons, our constructed etalon produces a sinusoidal structure closer to that associated with parasitic etaloning (i.e., unwanted fringing from parallel surfaces present in many optical systems). In fact, the quality of this etalon is so low that the cavity finesse, which is given by the ratio of the half-width of a transmission peak to the spectral range between peaks, is indefinable because the transmission does not drop below 0.66 (the half-width cannot be measured). In general, such a low quality etalon would not be of value in optical experiments. This is particularly true for frequency stabilization, because the transmission peaks are so broad that locking with suitable stabilization is not possible using conventional techniques, where the transmission peaks are used for locking. However, with use of wavelength modulation, the effective cavity finesse can be improved to a point that locking becomes possible.

To understand how locking is achieved using this technique, consider the etalon transmission spectrum when wavelength modulation spectroscopy is employed. Using the derivative approximation for the harmonic detection signals, the spectrum of each harmonic is shown in FIGS. 2a to 2d. Plots are shown of first through fourth harmonic, (a) through (d), respectively, for transmission through a low-quality Fabry-Perot etalon, with reflection coefficient of 10% and optical length of 23.4 mm. The scale on the x-axis is wavelength in meters and the scale on the y-axis is in arbitrary units. At the wavelengths that the transmission profile peaks (the Fabry-Perot resonances seen in FIG. 1), the even harmonics peak and the odd harmonics pass through zero. Due to their odd symmetry, the odd harmonics (first, third, fifth, etc.) can be used to stabilize the frequency of the laser through feedback of the harmonic signal. Stabilization with this technique locks the laser frequency to the peak transmission of the etalon.

There is an additional advantage for using wavelength modulation for laser stabilization. When the wavelength-modulated beam is locked to the zero crossing of the odd harmonics, only even harmonics are passed through the etalon. The structure of the even harmonics near this point is very similar to that of a high quality etalon. Thus, the even harmonics are used to effectively increase the finesse of the cavity, enhancing the filtering ability of the etalon. A comparison of the even harmonic signals with the direct transmission signal is shown in FIGS. 3a to 3d, where it is observed that the half-width of the peak signal decreases substantially with harmonic order for each of the four low-quality etalon cavities shown (reflective surfaces of 10%, 15%, 20%, 30%). The plots have been normalized to peak transmission, and the x-axis is wavelength in meters. This shows an improvement in the effective finesse or filtering ability of the cavity.

Table I shows a comparison of effective cavity finesse for direct, second, and fourth harmonics. The asterisk indicates that half-width cannot be defined since the transmission profile does not drop to 0.5 anywhere in the spectrum of interest; thus, cavity finesse cannot be defined for this etalon. The table quantifies the improvement for the four low-quality Fabry-Perot etalons, which shows that the improvement is largest for the lowest quality etalon. Thus, with use of this stabilization technique one can achieve the benefits of a higher quality etalon, without the additional expense of improving the etalon itself.

Resolution of Spectral Features

The sw-NIR region of the spectrum, 0.7-1.6 μm, has received a great deal of attention in the field of non-invasive detection, due to the availability of inexpensive optical sources and the potential for transmission through tissues. For example, see, J. Burmeister and M. Arnold, *Spectroscopic Considerations for Noninvasive Blood Glucose Measurements with Near Infrared Spectroscopy*, Leos Newsletter, April 1998; Kaoru Asano, *Introduction of Noninvasive Technology*, Sysmex Journal International, Vol. 9 No. 1 (1999); R. Anthony Shaw and Henry H. Mantsch, *Infrared Spectroscopy in Clinical and Diagnostic Analysis*, John Wiley & Sons Ltd.; R. W. Waynant and V. M. Chenault, *Overview of Non-Invasive Optical Glucose Monitoring Techniques*, Leos Newsletter, April 1998: Volume 12, number 2; T. Koo, A. Berger, I. Itzkan, G. Horowitz, and M. Feld, *Measurement of Glucose in Human Blood Serum Using Raman Spectroscopy*. Absorption from glucose in this region is attributed to extremely weak bands formed from overtones and combination tones of component vibrations. Measurements of these weak absorptive bands with path lengths on the order of 1cm require very sensitive optical probing techniques. Further, such measurements must have high spectral resolution in order to minimize the chances of over- or underestimation due to the presence of other constituents. Wavelength modulation spectroscopy is a measurement technique that can address these issues. The derivative nature of the harmonic detection signals amplifies small features of the absorption spectrum even if those features are broadband. Furthermore, because multiple harmonics are generated simultaneously, there is built-in redundancy for measurement verification.

Test Setup of Monitoring Device

Figure 4:
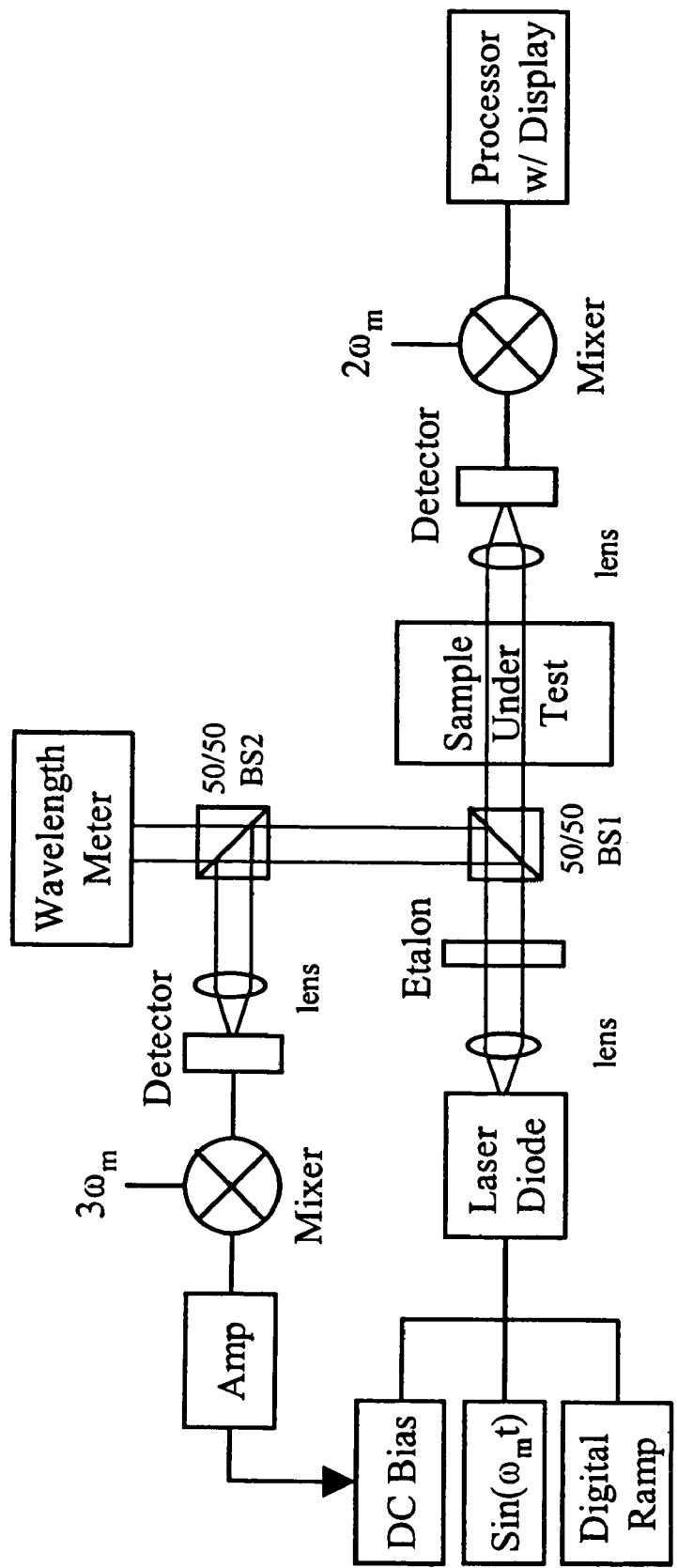
FIG. 4 shows a test setup for a blood glucose monitoring system using laser wavelength modulation spectroscopy in accordance with the present invention.
Figure 5A:
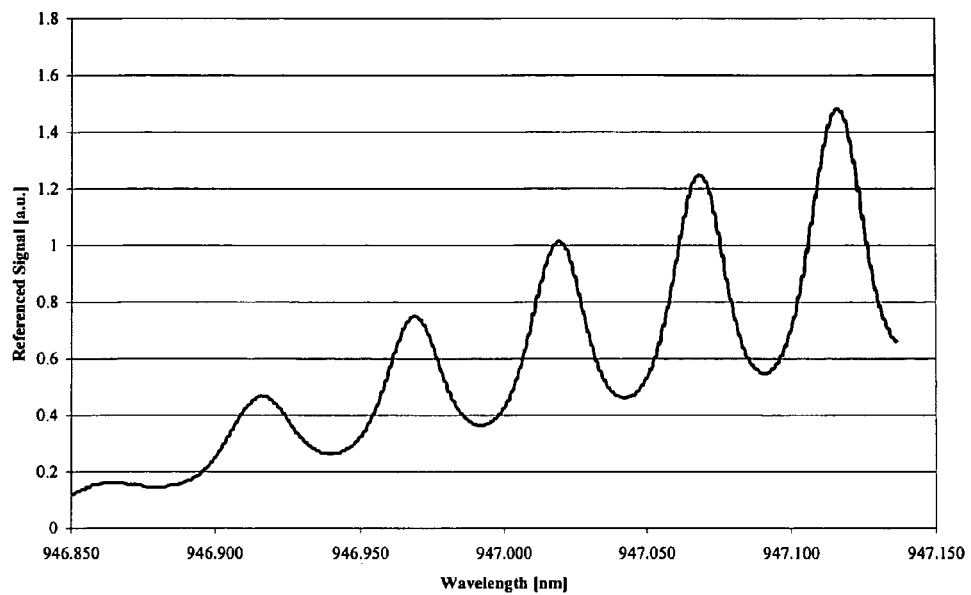
FIGS. 5a to 5e show direct and first to fourth harmonic wavelength modulation signals from transmission through a sample using a constructed etalon.
Figure 5B:
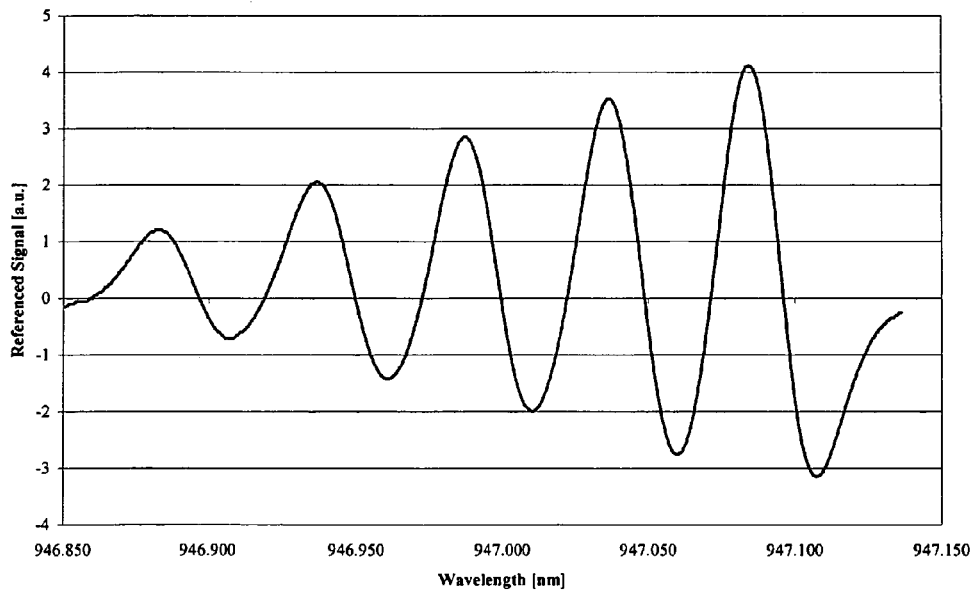
Figure 5C:
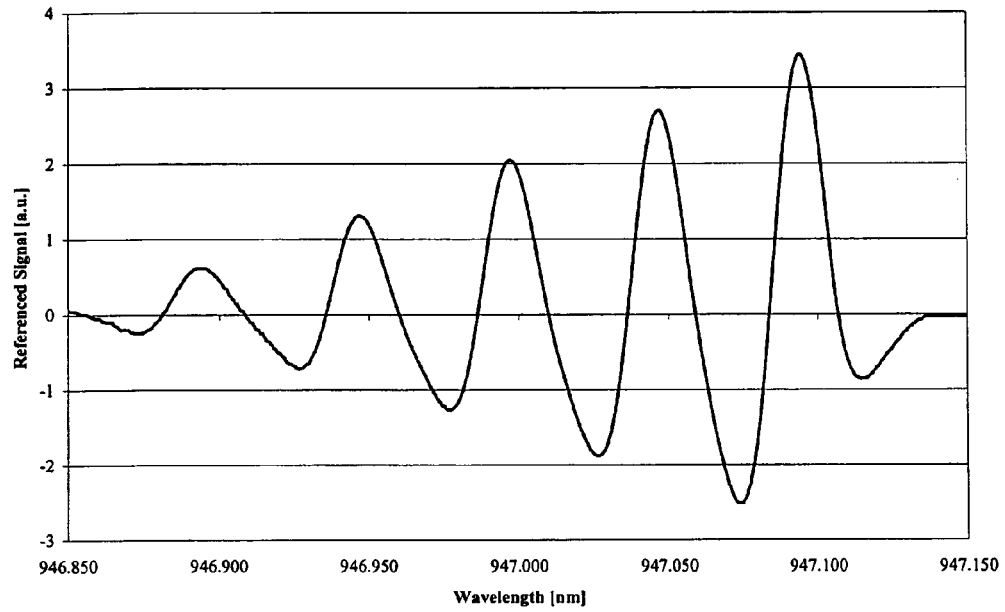
Figure 5D:
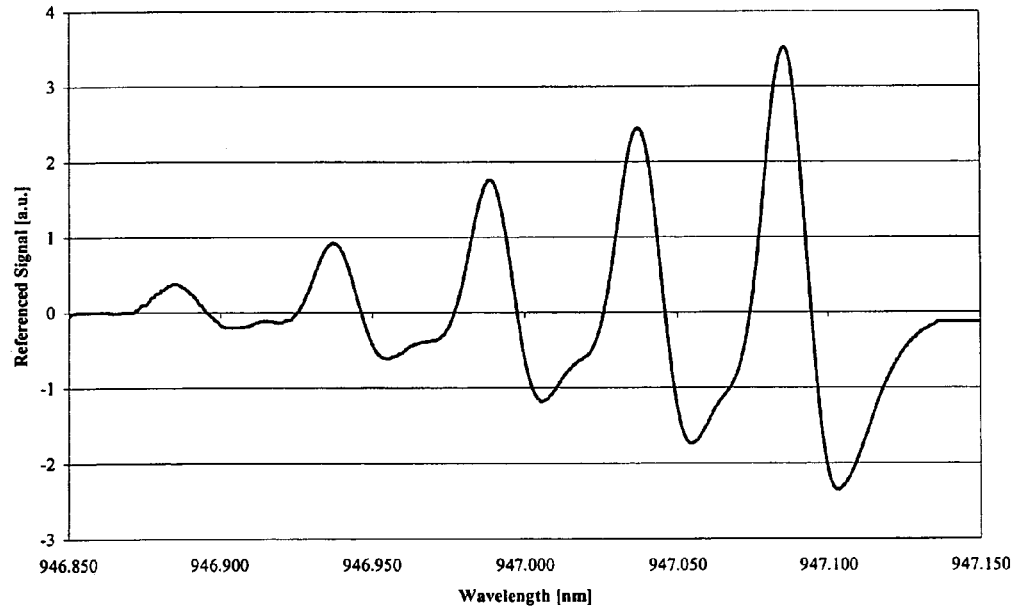
Figure 5E:
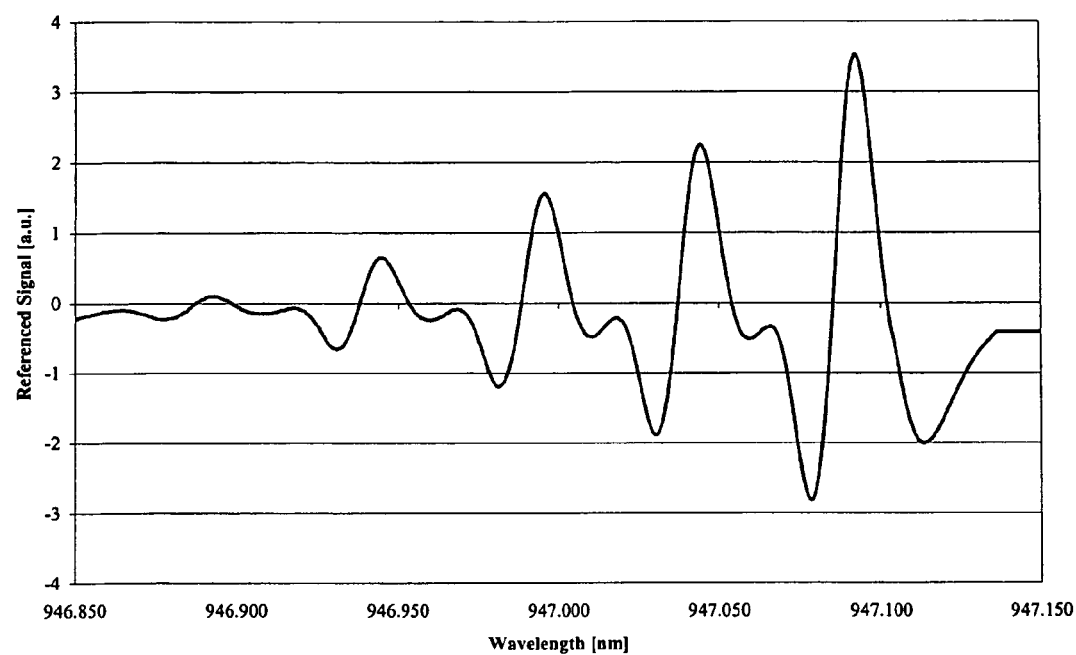

A test setup of a blood glucose monitoring system is shown in FIG. 4. The key components are a sw-NIR laser diode, a laser driver and with controlled feedback for stabilization, a Fabry-Perot etalon, sample interaction path, two photodetectors with mixers, and a processor with display. The laser, which is thermally stabilized, is brought above threshold by applying an appropriate dc bias and is wavelength modulated with a sinusoidal injection current. The wavelength of the diode is discretely incremented with a digital ramp from a microcontroller. The discrete steps of the digital ramp are chosen so the output wavelength of the laser corresponds to a transmission peak of the Fabry-Perot etalon. The laser is locked into each of these wavelengths with feedback of the demodulated third-harmonic signal resulting from the transmission profile of the Fabry-Perot etalon. The third harmonic signal is amplified to the appropriate level and summed with the dc bias. These four components, dc bias, sinusoidal modulation, step ramp, and feedback loop, constitute the laser-driver circuit.

A control solution is used as a reference to calibrate the system prior to measurement of the sample. Further, low-pass filtering of the feedback signal before mixing, provides a reference for the laser output intensity, allowing for compensation of source fluctuations and absolute measurements of concentration. The sample under test is probed at each transmission peak of the Fabry-Perot etalon over a target wavelength range of the constituent's spectral signature. Following the transmission through the sample, the probe beam containing the spectral signature of the sample under test is detected by the photodetector and demodulated at the second harmonic ($2\omega_m$) and the fourth harmonic ($4\omega_m$). The data are stored, processed, and displayed by the processor.

This setup is designed to maximize the signal-to-noise ratio, while reducing the processing time by incorporating active filtering. The filtering is accomplished with the Fabry-Perot etalon and coherent detection at the third harmonic. This allows rapid probing of the sample under test at predefined defined wavelengths within the spectral range of interest, while minimizing noise through frequency locking, spectral filtering, and coherent detection. This setup design is compatible with VCSELs, edge-emitting lasers, and external cavity lasers; therefore, is extremely versatile for applications in sensing of other constituents in the blood as well as in other liquids and solids.

The test setup was used to monitor glucose levels in an aqueous sample which were measured with a thermally stabilized, continuous wave VCSEL emitting at 940 nm. The laser was driven with a dc bias current of 1.5 mA and had average output power of 0.5 mW. The wavelength of the laser was tuned and modulated via injection current, with a modulation frequency of 4 kHz and modulation depth of 80 μA. The sample was probed at each transmission peak of the Fabry-Perot etalon over a target range of glucose spectral signature (925-945 μm). In the following, data are first given to demonstrate the frequency locking for laser stabilization using the low-quality Fabry-Perot cavity, then data are presented from measurements of glucose.

Laser Stabilization Results

FIGS. 5a to 5e show direct and wavelength modulation signals from transmission through the constructed etalon. The curves represent the direct transmission shown in (a) and first through fourth harmonics shown in (b) through (e), respectively. The transmission profiles result is from an 8.8 mm air-filled Fabry-Perot etalon with reflection coefficients of 30% for each face, which was used for frequency stabilization. As predicted, the harmonic detection signals follow the derivative structure of the etalon transmission profile, where the first and third harmonic pass through zero and the second and fourth harmonics peak at the Fabry-Perot resonances. Using the third harmonic of the etalon transmission profile, we established locking to the resonance frequencies of better than 100 MHz.

While the measured signals follow the derivative trend, there is a deviation from the predicted signal shape (shown in FIG. 2) that appears in the second through fourth harmonics. First, there is an intensity ramp present that results from the ramped current used to tune the wavelength. This creates some asymmetries in the profiles of the individual transmission peaks.

Second, there are effects of modulation broadening that spread the respective peak signals spectrally, causing them to overlap more than predicted by the simple derivative model. The third difference is that the first harmonic has an overall dc bias. This is caused by the amplitude modulation that accompanies the sinusoidal injection current and is the reason the first harmonic signal is not used to for frequency stabilization. Even with these differences, the laser is successfully locked at the Fabry-Perot etalon resonances to within 100 MHz.

Detection of Glucose Levels

Figure 6C:
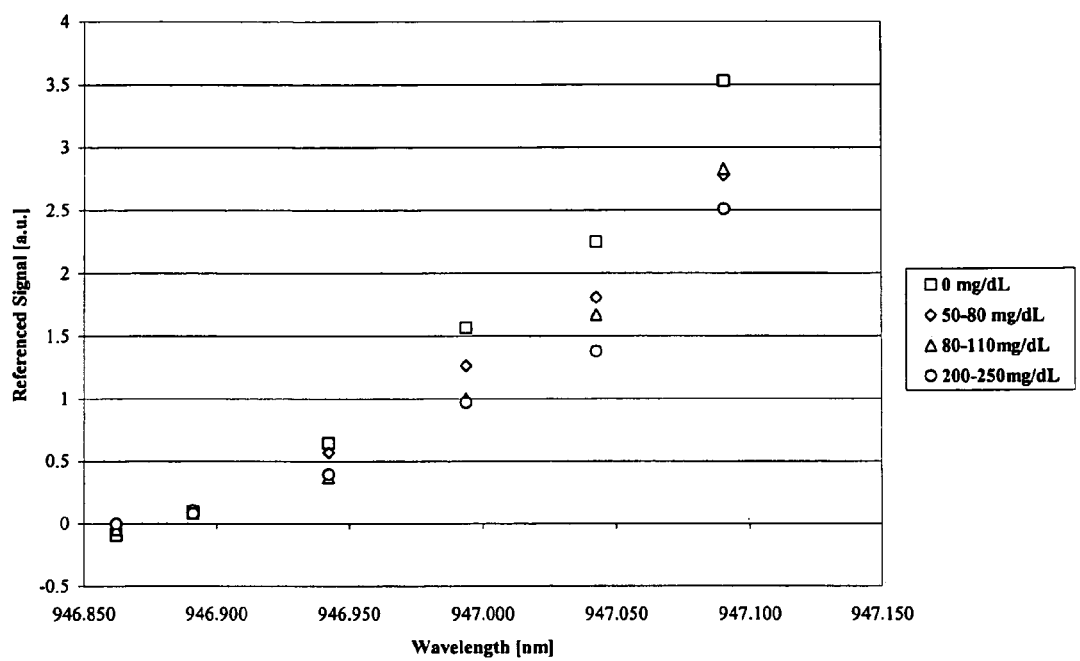
Figure 7A:
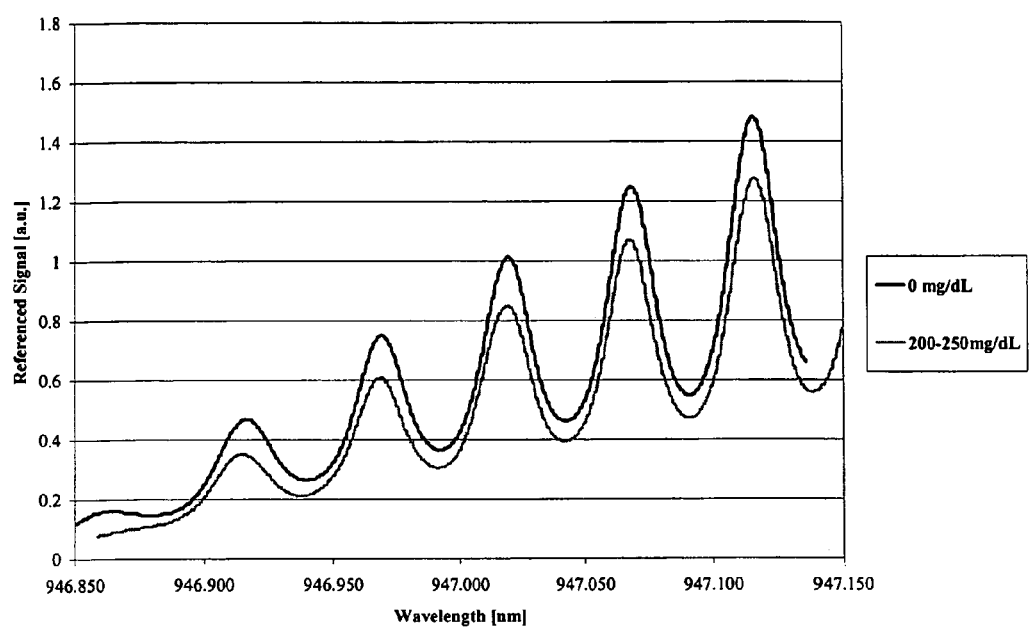
FIGS. 7a to 7e show comparisons of direct and first to fourth harmonic signals for a saline control and a glucose mixture from stepwise tuning through target resonant frequencies.
Figure 7B:
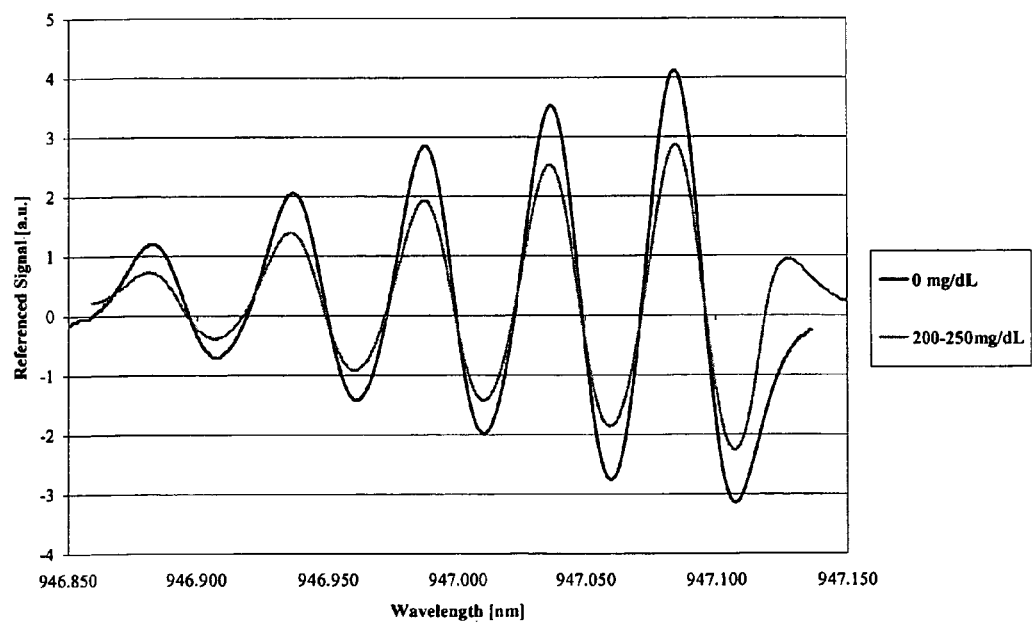
Figure 7C:
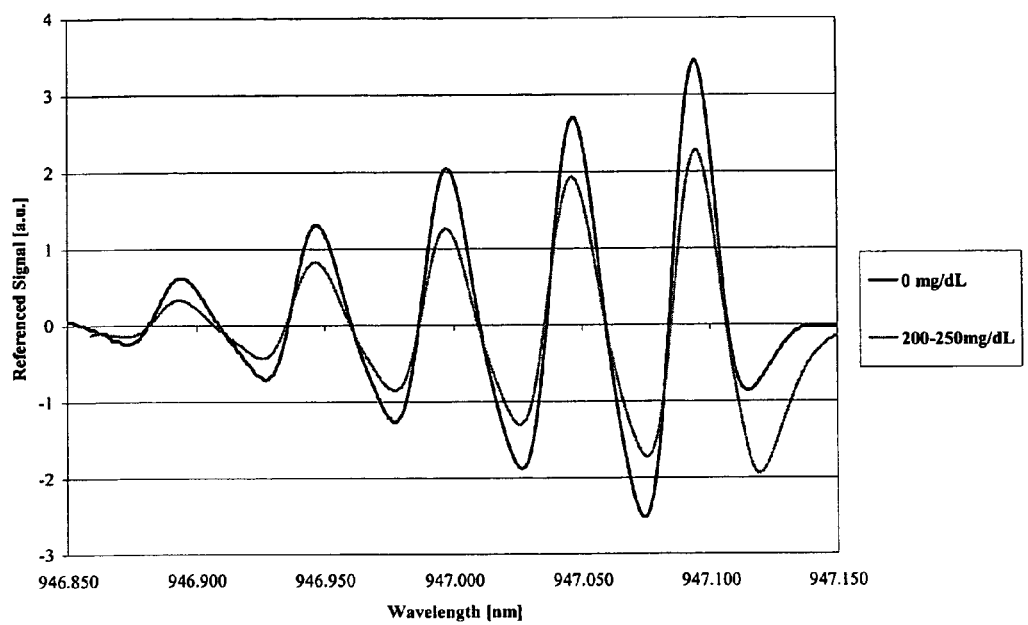
Figure 7D:
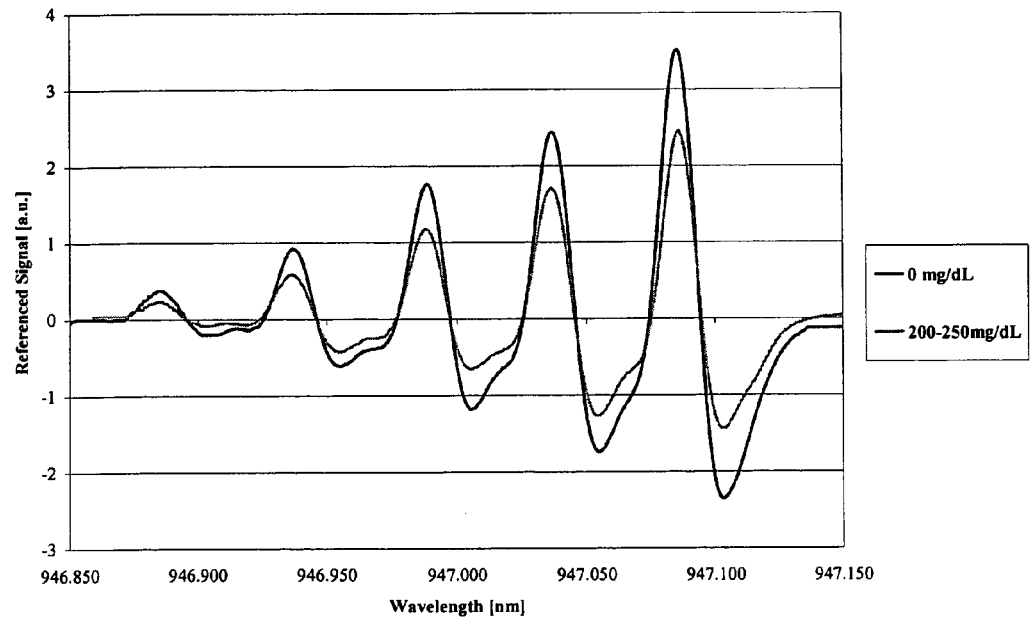
Figure 7E:
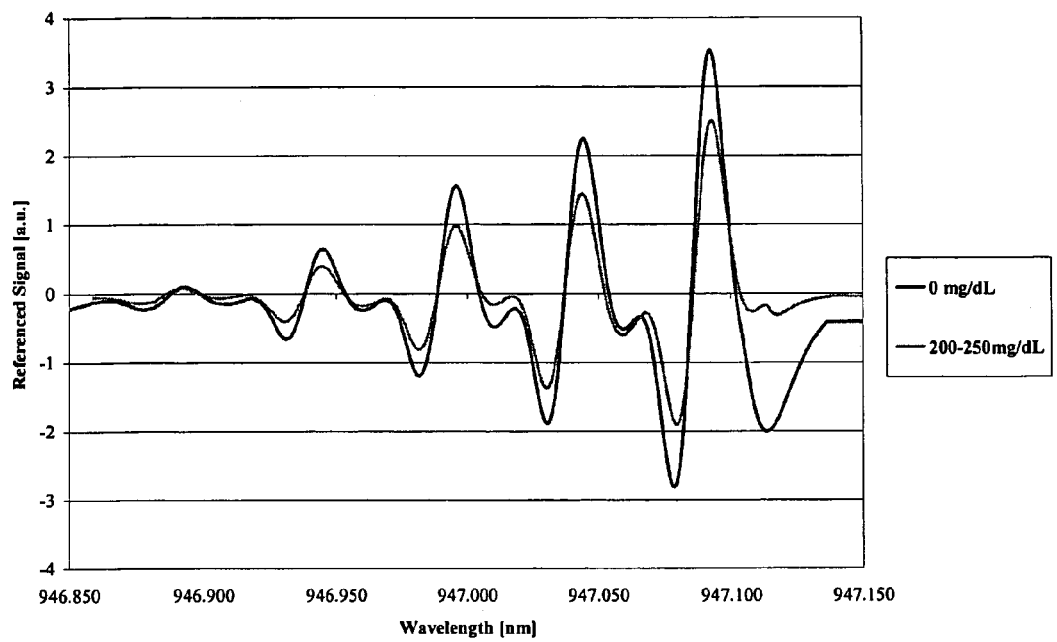

Aqueous samples containing glucose were prepared by dissolving dextrose in saline in a cuvette having 1 cm path length. This sample was probed using the test setup shown in FIG. 4 with the 940 nm VCSEL. The laser's center frequency was tuned and locked to the resonant frequencies of the etalon with feedback from the third harmonic signal. The absorption of each sample was measured at these resonant frequencies with the second harmonic and stored by a lock-in amplifier. The cuvette containing the glucose solutions was removed from the beam path and replaced with an identical cuvette that contained only pure saline. The measurements were repeated and stored by the lock-in amplifier. Comparisons of the results for direct, second, and fourth harmonic signals through a saline control and different levels of glucose mixtures are shown in FIGS. 6a to 6c. The data show marked differences between the samples throughout the measured spectrum. These differences can be effectively used to calibrate the system for assessing glucose concentrations in blood sample monitoring.

The absorption measurements for the glucose and saline samples were repeated to verify the observed differences throughout the measurement region and to confirm that the stepwise tuning (i.e., stepping through the spectrum at the resonant frequencies of the etalon) provided reliable data. In this repetition, the locking was omitted and the full spectrum was recorded. The etalon was kept in the test setup to provide visual verification of the spectral range measured. The glucose samples and the saline sample were probed with first through fourth harmonics and data are given for saline and one glucose mixture in FIGS. 7a to 7e. The signals for the glucose mixture are shown in gray line, and for pure saline are shown by solid black line for the total spectral range in FIG. 6. The presence of glucose is manifested in the differences between the harmonic signals for each of the sample solutions. This confirmed the fidelity of the measurement with the locking and demonstrated that the signal at the etalon's resonant peaks provides the best indication of glucose. Further, the relative difference in the signal for the various glucose concentrations was larger for the second harmonic signal when compared with the direct transmission signal. This is a primary benefit of the measurement technique employed in this system; the absorption signature is amplified by the derivative nature of the harmonic signals.

In general, absorption is correlated exponentially to the concentration of the absorbing species. Further, spectral absorbance profiles for species in solids and liquids are broadband and varied, having intricate nonlinearities. While for weak absorption, attenuation is linearly related to concentration, and over small regions of the spectrum the absorption profile can be considered linear, it is often not practical to use linear regression analysis with such measurements. For these reasons, we prefer a nonlinear regression to determine the proper algorithm for predicting glucose levels within the sample. A regression is used on the second and fourth harmonics at each measurement point within the spectrum, then an overall analysis of entire measured spectrum is performed for each concentration. The intersection of these regressions allows us to identify glucose (or other chosen constituent) from the background interference.

The results show a tremendous potential for non-invasive optical detection of glucose in the sw-NIR spectrum. The central novelty here is the application of wavelength modulation spectroscopy for both frequency stabilization (effective wavelength digitization) and enhancement of the spectral signature of glucose in a region where it is known to have exceedingly weak, broadband absorption features. The use of wavelength modulation was shown to allow the use of a very poor-quality Fabry-Perot etalon for frequency stabilizing a semiconductor laser. The third harmonic was used to lock to the resonance frequencies of the etalon and the second harmonic was use to probe the sample under test. Evidence of the presence of glucose in an aqueous state was demonstrated. The presence of glucose in the aqueous samples was seen at both second the fourth harmonic, providing measurement confirmation and redundancy as well as a means for compensating for any source fluctuations (by taking the ratio of second to fourth harmonics).

In a particular embodiment, the monitoring device can be used to monitor blood glucose concentrations from externally of the body and non-invasively, without the need to lance for a blood sample. As shown in FIG. 8, a laser probe 80 is used to transmit frequency modulated laser light harmlessly through a thin layer of skin, such as the earlobe or finger webbing, where it is attenuated by glucose in blood vessels and interstitial fluids in the skin SS. The transmitted light is detected by a photodetector 81, which relays the light detection data to a processor MPU where the data are spectrally analyzed, and processed (as described above) to measure quantitatively and accurately the patient's blood glucose concentration. In a miniaturized device, the laser probe and detector can be incorporated in an earlobe or skin clip and connected by a wire lead or wirelessly to a processor unit worn at hip level. The processor unit can then display the current blood glucose levels detected to the wearer of the device or relay this information to a physician or healthcare specialist. Because it is non-invasive, the device can continuously monitor blood glucose levels throughout the day and store the detected levels in a memory bank for recall at the user's convenience. The processor can also have a function to sound an alarm when glucose levels are such that the user requires administration of insulin.

The glucose spectrum has absorption bands in the shortwave near infrared (<1 um) that are not totally masked by water absorption, although they are the very weakest of the glucose bands. Tissue transmission within this range is fairly decent, with optical density (defined as $\log_{10}(1/\text{Transmission}))$ at less than 1.2 in the region of the ear. With most optical spectroscopy techniques, though, these weak glucose bands have not provided a substantial enough signature to determine blood-glucose levels with the same accuracy of the enzyme-based tests, and thus, have not been targeted features for such optical measurements. However, the invention provides an ultra sensitive optical sensing scheme based on laser spectroscopy to enable accurate detection of glucose using the weak bands that lie in the sw-NIR outside the strong water absorption spectrum. The measurement employs active signal processing to spectrally stabilize the source while also providing a means to optically measure the slopes of the glucose spectrum surrounding the probe wavelength, allowing for enhancement of the spectral signature and accurate detection of the blood-glucose levels. Through enhancement of the glucose signature, key features can be targeted with high resolution and interference from background species can be significantly reduced. Furthermore, the measurement system is simple in its design and employs semiconductor photonic components that are easily integrated with the system electronics, lending to overall system robustness. The radiation used is harmless to the tissue and causes no greater harm to the human eye than that used in a CD player.

The noninvasive glucose sensor can be calibrated to adjust for differences in soft tissues for patients of different ages, ethnicities, skin pigmentations, and diabetic conditions. When determining glucose concentrations, these adjustments can include: (a) effect of skin pigmentation; (b) effect of different hematocrit values; (c) effect of different blood types; (d) effect of environmental factors (room temperature, humidity); and/or (e) effect of physiological factors (body temperature, age, weight, etc.).

Figure 9A:
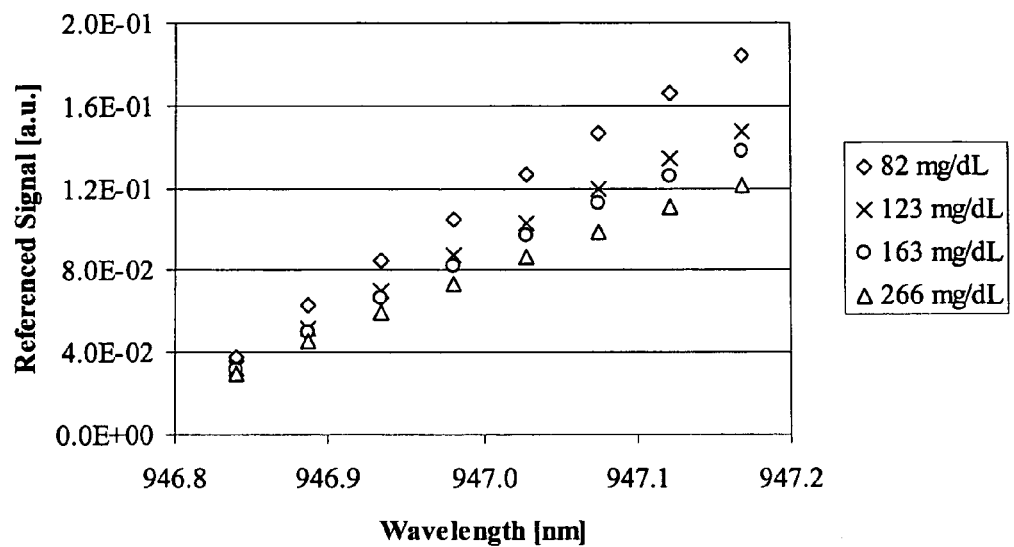
FIGS. 9a to 9c show comparisons of direct, second and fourth harmonic signals, respectively, obtained for varied concentrations of glucose in a whole blood sample.
Figure 9B:
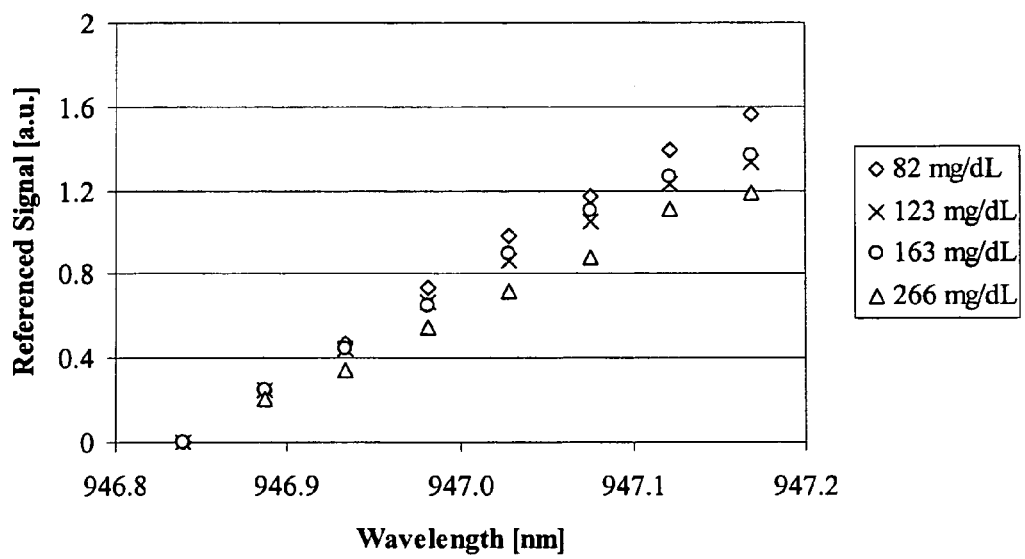
Figure 9C:
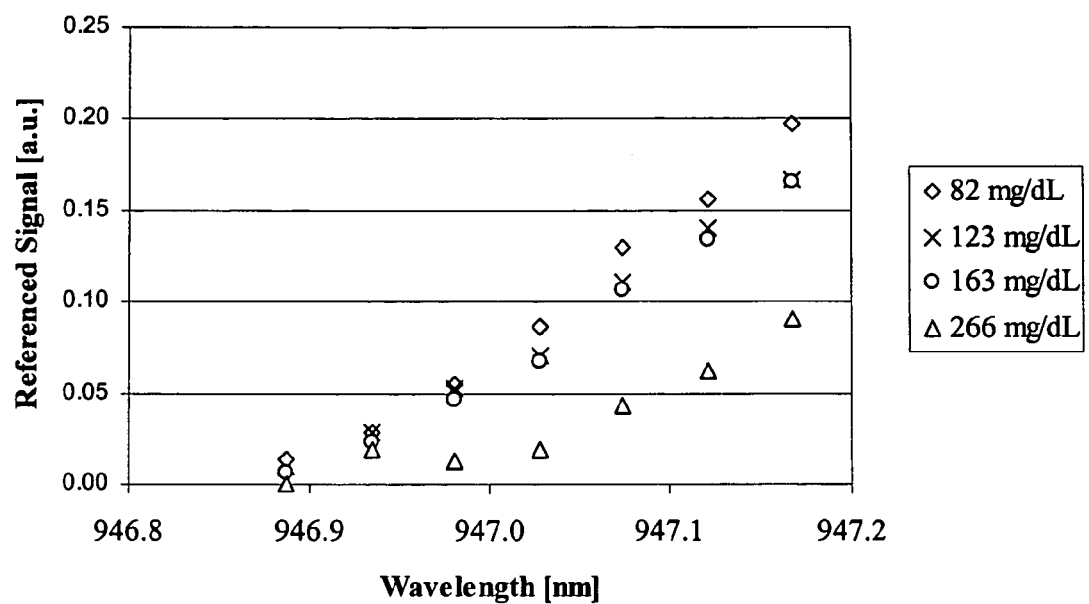

For non-invasive detection of blood glucose levels, the primary detection is done at second harmonic. When combined with source stability provided by the third harmonic, the detection technique was found to offer three primary advantages: (1) it enhances non-linear features to give stronger spectral indicators of glucose; (2) it inherently filters background noise; and (3) it reduces the required incoming data through discrete tuning and locking, which increases the computational measurement speed. FIGS. 9a to 9c show a sampling of direct and second and fourth harmonic data taken with the test setup. The results show a particularly consistent trend at second harmonic for varied concentrations of glucose in whole blood. As in the saline experiment, the laser was driven with a dc bias current of 1.5 mA and had average output power of 0.5 mW. The wavelength of the laser was tuned and modulated via injection current, with a modulation frequency of 4 kHz and modulation depth of 80 µA. Samples were made from whole blood and dextrose mixtures by the following procedure. A single blood sample was divided into two parts, part A and part B, each 3 mL in volume. Part A was mixed with dextrose such that the concentration of glucose in the blood was greater than 1000 mg/dL and was allowed to settle for several hours to thoroughly mix. Part B was used as the measurement sample, where upon each measurement a small portion of part A was infused into part B to increase the glucose concentration.

Figure 10:
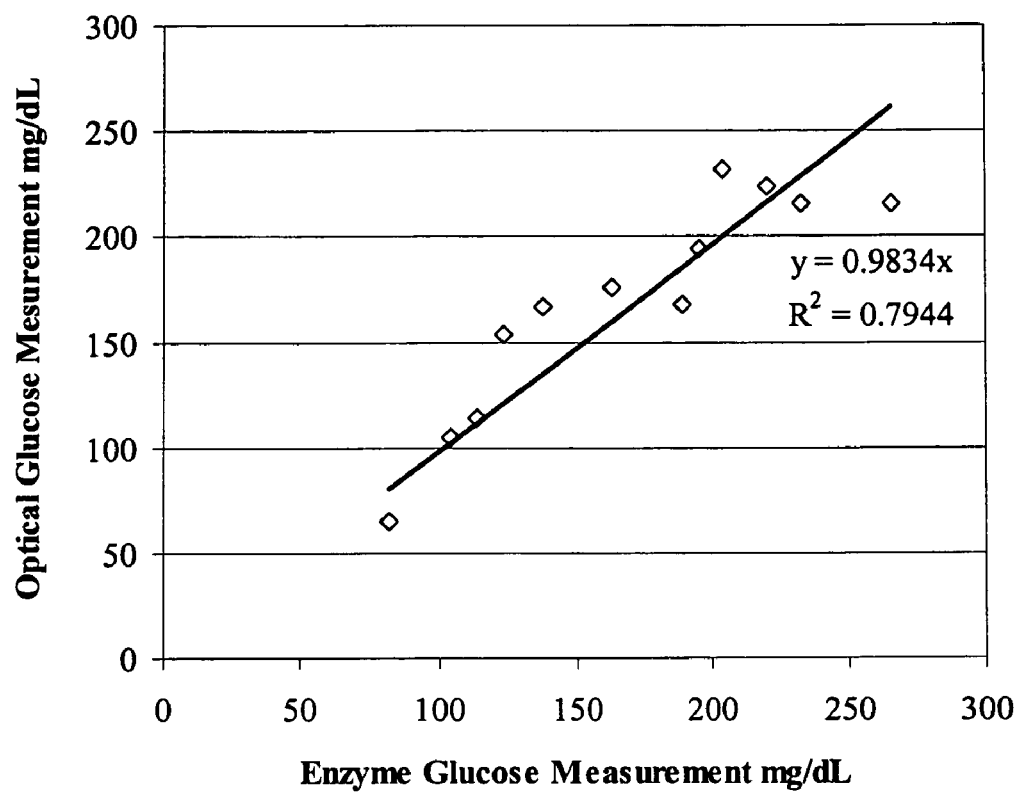
FIG. 10 shows a comparison of detection of blood glucose concentration using the optical monitoring system of the invention with a standard enzyme measurement test.

The sample (part B) was probed at each transmission peak of the Fabry-Perot etalon over a target range of glucose spectral signature (925-945 µm). The data show a similar behavior to that observed in the saline solutions, where an increase in glucose concentration of the sample decreases the received signal while maintaining the same spectral profile for 7 discrete data points. In FIGS. 9a to 9c, four concentrations of glucose are shown, which were then mapped to the actual glucose concentration to calibrate the system for future predictive measurements. FIG. 10 shows a comparison of optical glucose measurements against a standard enzyme based measurement with $R^2$ of approximately 0.8.

Figure 11:
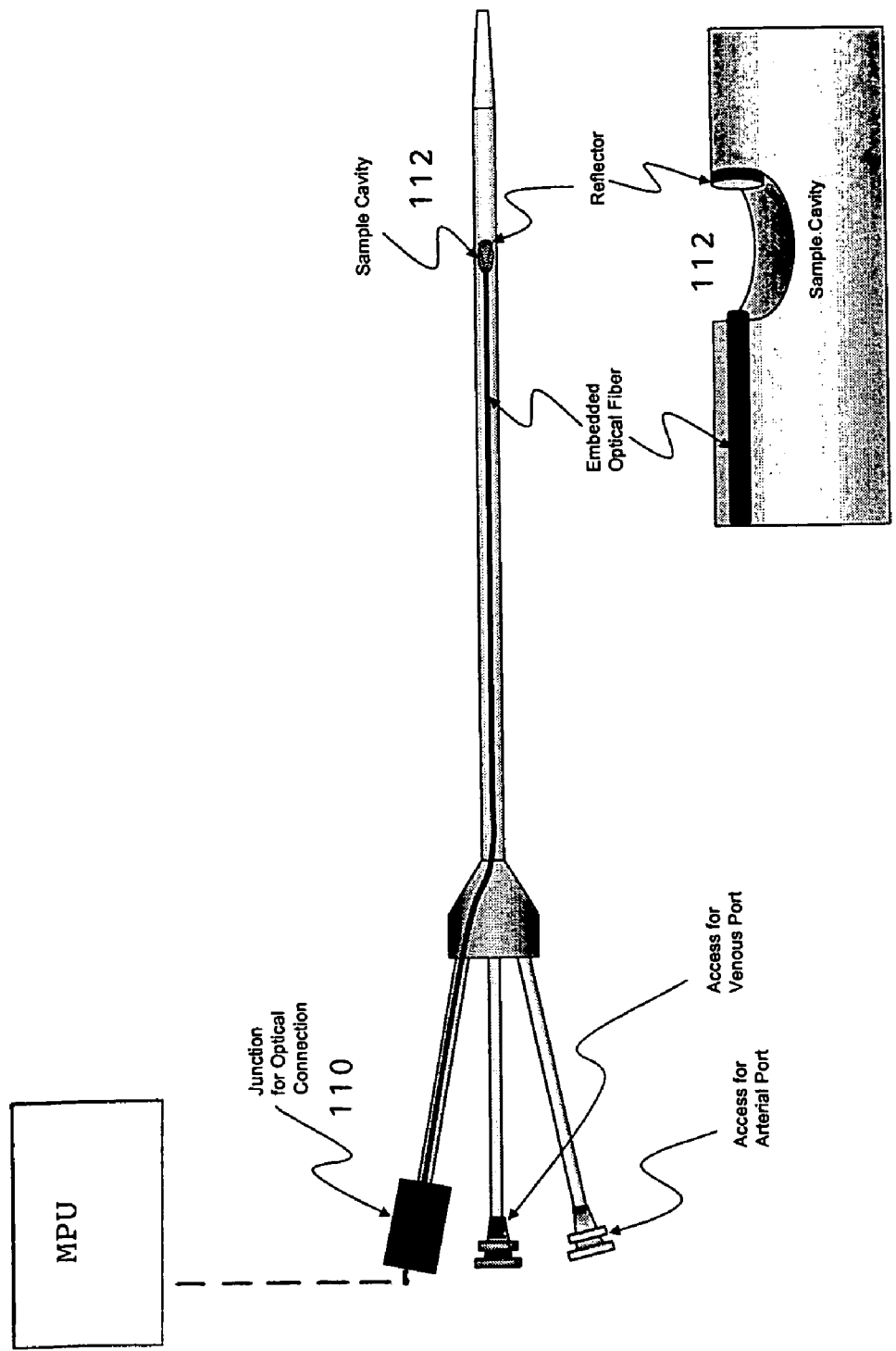
FIG. 11 illustrates an intravenous monitoring system in which laser light is transmitted through an intravenous blood sample and collected via an optical fiber inserted through a catheter probe.

In another particular embodiment, the monitoring device is used as an intravenous sensor for continuously monitoring blood glucose levels of patients through a catheter or other probe deployed intravenously. As shown in FIG. 11, a junction 110 is used for connection to a laser diode to deliver light through an optical fiber to a sample cavity 112 within a probe end of a catheter probe. The light is transmitted through a blood sample held in the sample cavity 112 to a reflector which returns the light back into the optical fiber for transmission to a photodetector connected via the junction 110. Since upon return, the light is propagating in the opposite direction from the source emission, it can be separated from the incident light with an optical circulating element or beam splitter. The light transmitted through the blood in contact with the probe cavity is collected by the photodiode and spectrally analyzed and processed by a processor MPU in seconds to measure the patient's blood glucose levels. It can be used to regulate blood glucose levels in critically ill patients who suffer from hyperglycemia, where self-regulation of glucose and insulin levels might otherwise fail or require constant nursing attention. The detection level output can be used to control an insulin pump to stabilize the patient's glucose concentration within a desired range, such as 80-110 mg/dL, which has been shown to reduce mortality, morbidity, blood infection, and renal failure for critically ill patients in an intensive care unit. See, Van den Berghe, G., et al., Outcome benefit of intensive insulin therapy in the critically ill: Insulin dose versus glycemic control, Critical Care Med., 2003. The device can similarly be used to monitor other blood constituents, such as carbon dioxide, hemoglobin, potassium, etc.

The device described herein is capable of continuously monitoring blood glucose so that the critically ill patient's blood chemistry can be controlled within the normal glucose levels of 80-110 mg/dL. Doing so can help prevent the onset of secondary effects of hypoglycemia often encountered in critical illness, where the body ceases to properly regulate glucose and insulin in the blood. Conventional treatments of adverse effects of a critical illness have involved continuous insulin infusions to maintain blood glucose levels. This requires a nurse extracting blood for enzymatic measurement on an hourly basis, which is very time consuming and costly from a personnel standpoint. Further, hourly regulation of insulin administration is insufficient to prevent trauma related spikes in glucose levels. The disclosed system is capable not only of continuous monitoring of blood glucose levels, but is also capable of controlling an insulin pump to regulate the patient's blood glucose level, thus greatly reduce the labor, cost, and error rate in conventional treatment of critical illness.

The principles of the invention are applicable in general to any region of the spectrum where tunable laser sources are available. Thus, this technique can be applied to drug detection, for example, or for health monitoring through detection of indicator constituents. Furthermore, because the apparatus employs a semiconductor laser source and absorption spectroscopy, the size and power requirements are minimal and the system is robust. Many of the components required to drive the laser source and demodulate the signal are commercially available in integrated chips, and therefore, the final system configuration can be compact and portable.

It is to be understood that many modifications and variations may be devised given the above description of the principles of the invention. It is intended that all such modifications and variations be considered as within the spirit and scope of this invention, as defined in the following claims.

TABLE I

| Reflection Coefficient | 10% | 15% | 20% | 30% |
|---|---|---|---|---|
| Direct Finesse | 1 * | 1 * | 1.41 | 2.26 |
| $2^{nd}$ Harmonic Finesse | 4.43 | 5.21 | 6.06 | 8.01 |
| $4^{th}$ Harmonic Finesse | 6.78 | 8.26 | 9.75 | 13.05 |
| Finesse Ratio $2^{nd}$/direct | 4.43 * | 5.21 * | 4.29 | 3.54 |
| Finesse Ratio $4^{th}$/direct | 6.78 * | 8.26 * | 6.91 | 5.77 |
| Finesse Ratio $4^{th}/2^{nd}$ | 1.53 | 1.58 | 1.60 | 1.62 |

The invention claimed is:

1. A device for monitoring the concentration level of a constituent in tissue or a body fluid sample comprising:
   (a) a laser light source in which the light is frequency modulated about a center emission frequency selected to probe a characteristic feature in an absorption spectrum of a constituent of the sample to be monitored;
   (b) a laser driver circuit, operatively coupled to said laser light source, for controlling the frequency modulation of the laser light and tuning the center emission frequency of the laser light through a desired region of the absorption spectrum of said constituent;
   (c) a photodetector for detecting light from the laser light source transmitted through the sample as the modulation emission frequency of the laser is tuned; and
   (d) a demodulator for demodulating the transmitted light and detecting variations in magnitude at harmonics of the modulation frequency so as to assess the concentration level of the constituent of the sample.

2. A device according to claim 1, wherein the laser light source is operated to pass the laser light through the sample as the modulation frequency is tuned about the center emission frequency, and light transmission signals are detected at a higher order harmonic to provide information on the absorber constituent of the sample.

3. A device according to claim 1, wherein the transmitted light detected by the photodetector is demodulated for higher order harmonics using phase-sensitive coherent detection.

4. A device according to claim 1, adapted for monitoring concentration of a constituent in bodily fluid non-invasively, wherein the laser light source and photodetector are positioned to provide trans-illumination through a thin layer of skin containing blood vessels.

5. A device according to claim 4, wherein the laser light source and photodetector are positioned on opposite sides of an earlobe or finger webbing to measure blood glucose concentration, without the need for physical penetration of the skin.

6. A device according to claim 1, adapted for monitoring concentration of a constituent in blood intravenously, wherein the laser light is transmitted and detected through an optical fiber in a catheter probe inserted intravenously into a patient's blood vessel.

7. A device according to claim 6, adapted for monitoring glucose concentration of blood in blood vessels, wherein the center modulation frequency is selected for monitoring the absorption spectrum of glucose in blood.

8. A device according to claim 7, wherein the transmitted light is spectrally analyzed and processed by a microprocessor to measure the patient's blood glucose levels, and used to control an insulin pump to stabilize the patient's glucose concentration within a desired range.

9. A device according to claim 1, adapted for monitoring blood glucose concentration, wherein the center modulation frequency of the laser light source is in the short wavelength near-infrared (sw-NIR) spectrum.

10. A device according to claim 1, wherein a Fabry-Perot etalon is used for stabilizing the modulation frequency of the laser light source.

11. A device according to claim 10, wherein the laser driver circuit is tuned and locked to the resonant frequencies of the etalon with feedback from the third harmonic signal of the selected modulation frequency.

12. A device according to claim 10, wherein a spectral signature of light transmission at a second harmonic of the selected modulation frequency is used to characterize the constituent of the sample being monitored.

13. A device according to claim 10, wherein a spectral signature of light transmission at a fourth harmonic of the selected modulation frequency is used to characterize the constituent of the sample being monitored.

14. A method for monitoring the concentration level of a constituent in tissue or a body fluid sample, comprising:
   (a) providing a laser light source for light modulated about a center emission frequency selected to probe a characteristic feature in an absorption spectrum of a constituent of the sample to be monitored;
   (b) tuning the center emission frequency of the laser light through a desired region of the absorption spectrum of said constituent;
   (c) detecting light from the laser light source transmitted through the sample as the modulation emission frequency of the laser light source is tuned; and
   (d) demodulating the transmitted light and detecting variations in magnitude at harmonics of the modulation frequency to assess the concentration level of the constituent of the sample being monitored.

15. A method according to claim 14, wherein the laser light source is operated to pass the laser light through the sample as the modulation frequency is tuned about the center emission frequency, and light transmission signals are detected at a higher order harmonic to provide information on the absorber constituent of the sample.

16. A method according to claim 14, wherein the transmitted light is demodulated for higher order harmonics using phase-sensitive coherent detection.

17. A method according to claim 14, used for monitoring concentration of a constituent in bodily fluid non-invasively, by trans-illumination through a thin layer of skin containing blood vessels.

18. A method according to claim 17, wherein the laser light is transmitted through a thin portion of a patient's skin, such as an earlobe or finger webbing, without the need for physical penetration of the skin.

19. A method according to claim 14, adapted for monitoring concentration of a constituent in blood intravenously, wherein the laser light is transmitted and detected through an optical fiber inserted through a catheter probe inserted intravenously into a patient's blood vessel.

20. A method according to claim 14, adapted for monitoring blood glucose concentration, wherein the center emission frequency of the laser light source is in the sw-NIR spectrum, and a second or fourth harmonic or a ratio of second to fourth harmonic of the modulation frequency is used to characterize the constituent of the sample being monitored.

* * * * *